US012631627B2

(12) United States Patent
Martin et al.

(10) Patent No.: US 12,631,627 B2
(45) Date of Patent: May 19, 2026

(54) SYSTEM AND METHOD FOR ANALYZING EXTRACELLULAR VESICLES WITH AN OPTICAL BIOSENSOR

(71) Applicant: Corning Incorporated, Corning, NY (US)

(72) Inventors: Gregory Roger Martin, Acton, ME (US); Allison Jean Tanner, Portsmouth, NH (US)

(73) Assignee: CORNING INCORPORATED, Corning, NY (US)

( * ) Notice: Subject to any disclaimer, the term of this patent is extended or adjusted under 35 U.S.C. 154(b) by 1094 days.

(21) Appl. No.: 17/296,723

(22) PCT Filed: Nov. 18, 2019

(86) PCT No.: PCT/US2019/061998
§ 371 (c)(1),
(2) Date: May 25, 2021

(87) PCT Pub. No.: WO2020/112408
PCT Pub. Date: Jun. 4, 2020

(65) Prior Publication Data
US 2022/0026425 A1 Jan. 27, 2022

Related U.S. Application Data

(60) Provisional application No. 62/773,753, filed on Nov. 30, 2018.

(51) Int. Cl.
| | |
|---|---|
| *G01N 33/543* | (2006.01) |
| *C12Q 1/04* | (2006.01) |
| *G01N 33/68* | (2006.01) |

(52) U.S. Cl.
CPC ......... *G01N 33/54373* (2013.01); *C12Q 1/04* (2013.01); *G01N 33/6872* (2013.01)

(58) Field of Classification Search
None
See application file for complete search history.

(56) References Cited

U.S. PATENT DOCUMENTS

| | | | |
|---|---|---|---|
| 4,815,843 A | 3/1989 | Tiefenthaler et al. | |
| 5,738,825 A | 4/1998 | Rudigier et al. | |
| 7,057,720 B2 | 6/2006 | Caracci et al. | |
| 7,136,550 B2 | 11/2006 | Mozdy | |
| 7,203,386 B2 | 4/2007 | Krol et al. | |
| 7,239,395 B2 | 7/2007 | Gollier | |
| 7,286,221 B2 | 10/2007 | Caracci et al. | |
| 7,292,333 B2 | 11/2007 | Fontaine et al. | |
| 7,346,233 B2 | 3/2008 | Gollier et al. | |
| 7,604,984 B2 | 10/2009 | Frutos et al. | |
| 8,114,348 B2 | 2/2012 | Caracci et al. | |
| 9,823,737 B2 | 11/2017 | Mazed et al. | |
| 9,835,626 B2 | 12/2017 | Schroit et al. | |
| 9,932,635 B2 | 4/2018 | Wong et al. | |
| 9,958,448 B2 | 5/2018 | Halbert et al. | |
| 2003/0118636 A1* | 6/2003 | Friesen ................ A61K 9/1271 | |
| | | | 435/325 |
| 2006/0110594 A1 | 5/2006 | Frutos et al. | |
| 2006/0141527 A1 | 6/2006 | Caracci et al. | |
| 2010/0062461 A1 | 3/2010 | Cen | |
| 2014/0141986 A1 | 5/2014 | Spetzler et al. | |
| 2016/0004298 A1* | 1/2016 | Mazed .................... H04N 5/33 | |
| | | | 345/633 |
| 2016/0298200 A1 | 10/2016 | Nazarenko et al. | |
| 2016/0334402 A1 | 11/2016 | Bosio et al. | |
| 2017/0045451 A1 | 2/2017 | Nolan et al. | |
| 2017/0097352 A1 | 4/2017 | Taylor et al. | |
| 2018/0067134 A1 | 3/2018 | Cicchetti et al. | |

FOREIGN PATENT DOCUMENTS

| | | |
|---|---|---|
| CN | 103197066 A | 7/2013 |
| CN | 106906294 A | 6/2017 |
| EP | 3093664 A1 | 11/2016 |
| WO | 2016/172226 A1 | 10/2016 |
| WO | 2017/053516 A1 | 3/2017 |
| WO | 2017/062901 A2 | 4/2017 |
| WO | 2017/066390 A1 | 4/2017 |

(Continued)

OTHER PUBLICATIONS

Deschout et al.(Nanoscale 6:1741-7 (Year: 2014).*
Bjorge, et al, "Extracellular Vesicles, Exosomes and Shedding Vesicles in Regenerative Medicine—A New Paradigm for Tissue Repair", Biomater. Sci., vol. 6, 2018, pp. 60-78.
Cha, et al, "Efficient Scalable Production of Therapeutic Microvesicles Derived From Human Mesenchymal Stem Cells", Scientific Reports, 8, No. 1171, 2018, pp. 1-16.
Ibsen, et al, "Rapid Isolation and Detection of Exosomes and Associated Biomarkers From Plasma", ACS Nano, vol. 11, 2017, pp. 6641-6651.
Jeong, et al, "Integrated Magneto-Electrochemical Sensor for Exosome Analysis", ACS Nano, vol. 10, 2016, pp. 1802-1809.

(Continued)

*Primary Examiner* — Christopher M Gross
(74) *Attorney, Agent, or Firm* — Chandra J. Duncan

(57) ABSTRACT

Various implementations of a system and method for analyzing extracellular vesicles (EVs) are disclosed having a number of innovative features. In one implementation, a method for analyzing EVs includes binding EVs to an optical waveguide biosensor and phenotyping the bound EVs. Phenotyping can include binding a labeled ligand to the EVs and/or rupturing the EVs and analyzing their cargo. In another implementation, a system for analyzing EVs includes EVs bound to an optical waveguide biosensor and a labeled ligand bound to the EVs. In another implementation, a kit for analyzing EVs includes a micro plate having wells containing optical waveguide biosensors functionalized with a binding agent configured to bind to EVs and at least one of: (a) labeled ligands configured to bind to the extracellular vesicles or (b) a reagent configured to rupture the extracellular vesicles.

19 Claims, 7 Drawing Sheets

(56) References Cited

FOREIGN PATENT DOCUMENTS

| WO | 2017/072360 | A1 | 5/2017 |
| WO | 2017/093466 | A1 | 6/2017 |
| WO | 2017/102902 | A1 | 6/2017 |
| WO | 2017/124000 | A1 | 7/2017 |
| WO | 2017/129662 | A1 | 8/2017 |
| WO | 2017/136676 | A1 | 8/2017 |
| WO | 2017/148785 | A1 | 9/2017 |
| WO | 2017/154951 | A1 | 9/2017 |
| WO | 2017/178472 | A1 | 10/2017 |
| WO | 2017/197399 | A1 | 11/2017 |
| WO | 2017/198695 | A1 | 11/2017 |
| WO | 2017/204187 | A1 | 11/2017 |
| WO | 2018/011191 | A1 | 1/2018 |
| WO | 2018/076018 | A1 | 4/2018 |
| WO | 2018/106648 | A1 | 6/2018 |

OTHER PUBLICATIONS

Li et al; "Progress in Exosome Isolation Techniques"; Theranositcs, 7 (3) 2017; pp. 789-804.

Oliveira-Rodriguez, et al, "Development of a Rapid Lateral Flow Immunoassay Test for Detection of Exosomes Previously Enriched From Cell Culture Medium and Body Fluids", Journal of Extracellular Vesicles, vol. 5, Issue 1, 2016, pp. 1-10.

Raghu, et al, "Nanoplasmonic Pillars Engineered for Single Exosome Detection", PLoS One, vol. 13 No. 8, E0202773; pp. 1-13.

Wei, et al, "Detection of Exosomal Biomarker By Electric Field-Induced Release and Measurements (EFIRM)", Biosens Bioelectron; vol. 44, 2013, pp. 13.

Wu, et al, "Isolation of Exosomes From Whole Blood by Integrating Acoustics and Microfluidics", PNAS, vol. 114 No. 40, 2017, pp. 10584-10589.

Yanez-Mo, et al, "Biological Properties of Extracellular Vesicles and Their Physiological Functions", Journal of Extracellular Vesicles; No. 4: 27066, 2015, pp. 1-60.

Chinese Patent Application No. 201980079331.X, Office Action dated Sep. 27, 2023, 6 pages (English Translation only), Chinese Patent Office.

Braekmans et al., " On-chip light sheet illumination enables diagnostic size and concentration measurements of membrane vesicles in biofluids", , In Nanoscale, Apr. 30, 2014 , pp. 0lb-009, XP055669222, United Kingdom.

International Search Report and Written Opinion of the International Searching Authority; PCT/US2019/061998; dated Feb. 24, 2020; 9 pages; European Patent Office.

Loozen et al., "On-chip optical trapping of extracellular vesicles using box-shaped composite SiO2-Si3N4 waveguides", In Optic Express, vol. 26, No. 21, Oct. 15, 2018 , p. 26985, XP055668756.

Rupert et al., "Effective Refractive Index and Lipid Content of Extracellular Vesicles Revealed Using Optical Waveguide Scattering and Fluorescence Microscopy", In Langmuir, vol. 34, No. 29, Jun. 20, 2018, pp. 8522-8531, XP055668478.

* cited by examiner

SYSTEM AND METHOD FOR ANALYZING EXTRACELLULAR VESICLES WITH AN OPTICAL BIOSENSOR

CROSS-REFERENCE TO RELATED APPLICATION

This is a national stage application under 35 U.S.C. § 371 of International Application No. PCT/US2019/061998, filed Nov. 18, 2019, which claims the benefit of priority under 35 U.S.C. § 120 of U.S. Provisional Application Ser. No. 62/773,753 filed on Nov. 30, 2018, the contents of which are relied upon and incorporated herein by reference in their entirety.

TECHNICAL FIELD

This relates to systems and methods for analyzing extracellular vesicles using optical biosensors, and especially systems and methods for purifying, phenotyping, and quantitating extracellular vesicles using optical biosensors.

BACKGROUND

Extracellular vesicles (EVs) are a heterogeneous population of membrane-enclosed vesicles. EVs are recognized as important components in cell-to-cell communication and are involved in numerous biological and pathological processes. EVs have been implicated in the development and progression of diseases, which has formed the basis for the use of EV analysis in a clinical setting. As the interest in EVs has increased, techniques have been developed to characterize them. These techniques characterize different features of EVs such as the size distribution, enumeration, protein composition, and intravesicular content.

Despite the development of these techniques, it is still a major challenge to isolate and/or differentiate various EVs. For example, conventional methods such as ultracentrifugation require highly specialized equipment that is not available in many laboratories and subject EVs to extreme forces that can damage them. Methods such as ultrafiltration, which rely on membranes having a specific molecular weight cutoff or pore size, can lead to EV loss due to non-specific binding of the EVs to the membrane materials. Methods involving precipitation of EVs often produce results that are contaminated with proteins or other molecules. Methods involving chromatography columns, which separate EVs based on affinity, size exclusion, or ion exchange, are laborious and time-consuming. Methods using microfluidic devices have very low throughput.

It would be desirable to develop characterization techniques that are easier to use and/or provide better results. It would be especially desirable to develop techniques that can be used to both isolate and analyze EVs in a microplate format.

SUMMARY

A number of methods are disclosed for analyzing or assaying extracellular vesicles (EVs) using optical biosensors, particularly optical waveguide biosensors. The methods can be used to purify the EVs and/or analyze a variety of characteristics of the EVs. For example, the methods can be used to quantify and/or identify EVs in a sample medium, especially those having one or more specific markers. The methods can be implemented using suitable EV analysis systems. In one implementation, an EV analysis system includes an optical reader configured to receive and analyze a microplate having a number of wells where each well includes an optical waveguide biosensor.

The methods and corresponding systems can be implemented in various ways to realize one or more of the following potential advantages. One advantage is that the EVs can be isolated, purified, and analyzed while bound to the surface of the optical waveguide biosensor, which makes these processes simpler and easier. Another advantage is that when binding agents (e.g., antibodies) specific for known EV surface markers or receptors are used to bind the EVs to the surface of the optical waveguide biosensor the EVs can be captured and phenotyped in a single step. Another advantage is that the EV analysis system can be implemented using microplates, which makes it easy to adopt due the prevalence of microplate handling equipment in most laboratories. Another advantage is that the EVs can be analyzed on a high-throughput basis.

One innovative aspect of the EV analysis methods can be implemented by using binding agents specific to certain EV surface markers to bind the EVs to the surface of the optical waveguide biosensor. The binding agents can be selected to capture only those EVs having the target marker. In this way, the process of binding the EVs to the optical waveguide biosensor can be used to separate EVs of interest from the rest of the sample medium including other EVs lacking the target marker. This allows the EVs to be phenotyped direct from the sample with no labels.

Another innovative aspect of the EVs analysis methods can be implemented by performing additional phenotyping analyses of the EVs after they are have been bound to the optical waveguide biosensor. Such additional analyses can include quantifying the EVs, classifying and separating the EVs based on the presence or absence of one or more additional markers, and/or analyzing the intravesicular content of the EVs.

In one implementation, the quantity of EVs in a sample or bound to the surface of the optical waveguide biosensor can be determined by comparing the measurements of the sample to the measurements of one or more samples having a known quantity of the same EVs or EVs having the same marker(s). For example, a standard curve can be created using samples having known quantities of specific EVs and compared to the curve produced by samples having an unknown quantity of the same EVs (or EVs with the same marker(s)) to determine the quantity of EVs in the unknown samples.

In another implementation, the EVs can be further analyzed by binding one or more labeled ligands to additional marker(s) or receptor(s) present on the EVs. The ligands can be labeled with a fluorescent label, colorimetric label, and/or a luminescent label. The labeled ligands can be used to further characterize the type of EVs bound to the surface of the optical waveguide biosensor.

In another implementation, the intravesicular content of the bound EVs can be analyzed. This can be done by rupturing the EVs using an appropriate reagent and analyzing the contents, which can include proteins, DNA, and/or RNA. In one implementation, the EVs can be ruptured using a lysing reagent such as TRIzol and the like.

It should be noted that the term "phenotype" refers to the observable characteristics of the EVs at any level—physical, morphologic, biochemical, or molecular.

The systems, methods, and devices of this disclosure each have several innovative aspects, no single one of which is solely responsible for the described desirable attributes. The summary is provided to introduce a selection of concepts in a simplified form that are further described below in the detailed description. The summary and the background are not intended to identify key concepts or essential aspects of the disclosed subject matter, nor should they be used to constrict or limit the scope of the claims. For example, the scope of the claims should not be limited based on whether the recited subject matter includes any or all aspects noted in the summary and/or addresses any of the issues noted in the background.

DRAWINGS

The preferred and other implementations are disclosed in association with the accompanying drawings in which.

DETAILED DESCRIPTION

EV Analysis System

Figure 1:
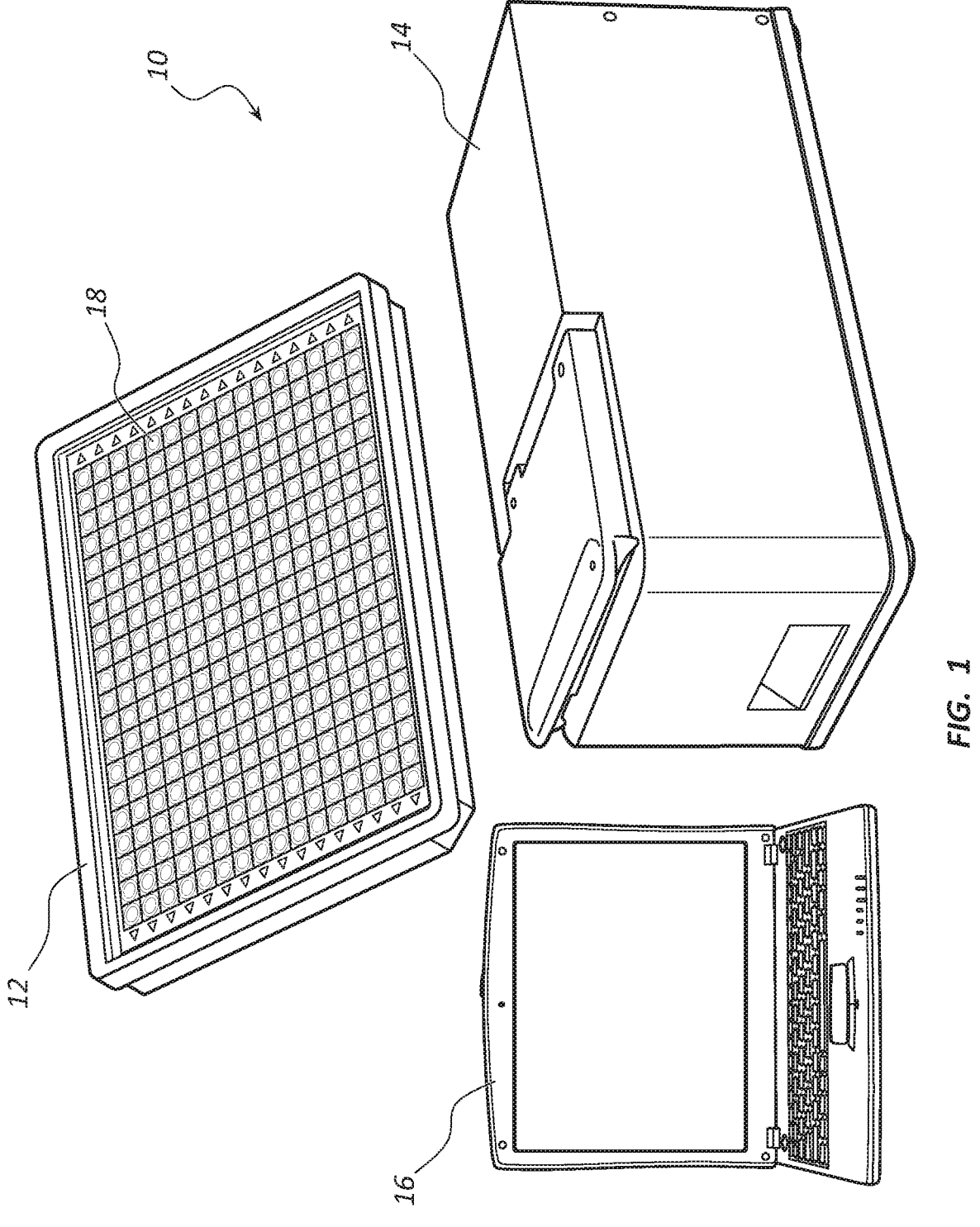
FIG. 1 is a perspective view of a system for analyzing extracellular vesicles (EVs) in accordance with embodiments of the present disclosure.

Referring to FIG. 1, a perspective view of a system 10 for analyzing extracellular vesicles (EVs) is shown (alternatively referred to as an EV analysis system or an EV assay system). The system 10 includes a microplate 12 an optical reader 14 (alternatively referred to as an optical plate reader) and a laptop computer 16. The microplate 12 is configured to hold samples containing EVs. The optical reader 14 is configured to analyze the samples in the microplate 12. The computer 16 includes software for instrument operation and data analysis. The computer 16 can be used to control the operation of the optical reader 14 and other related laboratory equipment.

The system 10 can be configured to have any suitable sample throughput. In some implementations, the system 10 can be considered a high throughput system (HTS) capable of measuring hundreds or even thousands of wells over an 8 hour period. For example, the system 10 can be configured to measure at least 500 wells in an 8 hour period, at least 1,000 wells in an 8 hour period, at least 2,000 wells in an 8 hour period, at least 3,000 wells in an 8 hour period, at least 4,000 wells in an 8 hour period, or at least 5,000 wells in an 8 hour period.

In high throughput implementations, the system 10 can be configured to be easily integrated with other equipment that facilitates rapid handling and analysis of large numbers of the microplates 12. The additional equipment can include a liquid handling system, a scheduler, and the like. In these implementations, much if not all of the operation of the system 10 can be automated.

FIG. 1 shows the optical reader 14 and the computer 16 being separate components. However, it should be appreciated that in other implementations the optical reader 14 and the computer 16 can be combined into a single unit. Numerous other changes can be made to the configuration of the optical reader 14 and the computer 16.

Microplate

The microplate 12 (alternatively referred to as a microwell plate or multiwell) is a generally flat plate having multiple wells 18 that function as small test tubes. Each well 18 includes an optical waveguide biosensor 20 integrated in the bottom of the well 18. The microplate 12 shown in FIG. 1 includes 384 wells 18.

It should be appreciated, however, that the microplate 12 can include any suitable number of wells 18 arranged in any suitable manner. For example, the microplate 12 can include 6, 12, 24, 48, 96, 384, 768, or 1536 of the wells 18. Also, the wells 18 can be arranged in a variety of ways such as in a 2:3 rectangular matrix.

Each of the wells 18 can be configured to hold various amounts of liquid ranging from nanoliters to milliliters. As a general rule, the size of the wells 18 decreases as the number of the wells 18 on the microplate 12 increases. It should be appreciated this is not a hard and fast rule. There can be situations where the microplate 12 has a small number of small wells 18 or a large number of large wells 18.

The wells 18 can also have any suitable shape and be made of any suitable material. In some implementations, the wells 18 can be circular, square, polygonal, and the like. In some implementations, the wells 18 can be made, at least in part, of polystyrene, polypropylene, polycarbonate, cyclo-olefins, metal, glass, ceramic, quartz, and the like.

The microplate 12 can have any suitable configuration provided that it is capable of holding the samples. In some implementations, the microplate 12 is built in accordance with the standard specifications set by the Society for Biomolecular Screening (SBS), for example the SBS-standard 384-well specifications.

Optical Waveguide Biosensor

Figure 3:
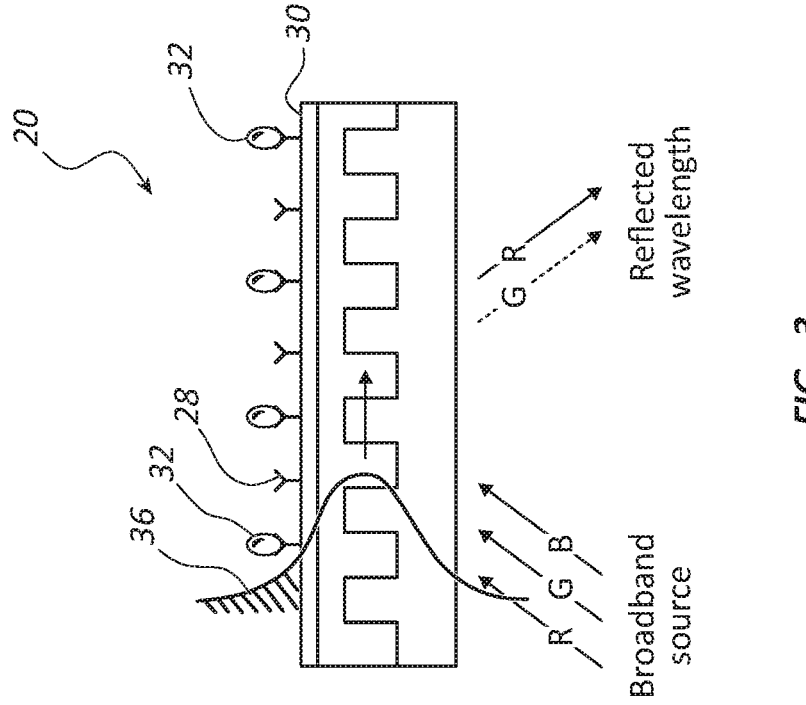
FIG. 3 is a cross-sectional view of the optical waveguide biosensor in FIG. 2 with EVs bound to the binding agent in accordance with embodiments of the present disclosure.
Figure 2:
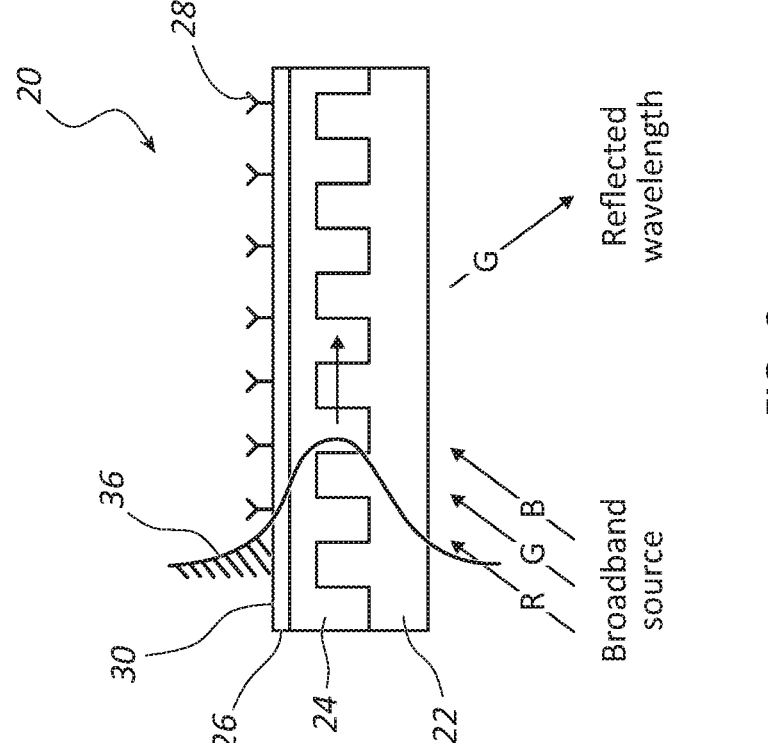
FIG. 2 is a cross-sectional view of an optical waveguide biosensor with a binding agent on the top surface in accordance with embodiments of the present disclosure.

Referring to FIGS. 2-3, cross-sectional views of one implementation of the optical waveguide biosensor 20 are shown. The optical waveguide biosensor 20 includes a substrate layer 22, a waveguide layer 24 (alternatively referred to as a waveguide coating or waveguide thin film) on the substrate layer 22, and a surface chemistry layer 26 (alternatively referred to as a binding layer or binding surface) on the waveguide layer 24. The substrate layer 22 includes an optical grating embedded in a substrate material such as glass. The waveguide layer 24 is a dielectric material having a high index of refraction.

It should be appreciated that the optical waveguide biosensor 20 can be any suitable type of waveguide biosensor having any suitable configuration. For example, the optical waveguide biosensor 20 can be a single mode or multimode optical waveguide biosensor. It can also include any suitable type of waveguide such as a resonant waveguide grating, nanostructured optical grating, planar waveguide, and the like. The optical grating can be embedded in the substrate layer 22, waveguide layer 24, or at the interface of the layers 22, 24. In one implementation, the optical waveguide biosensor 20 is an optical resonant waveguide grating biosensor (RWG biosensor).

The surface chemistry layer 26 includes a thin layer of surface chemistry (alternatively referred to as binding chemistry) that provides an active surface 30 on the top of the optical waveguide biosensor 20 for attachment and immobilization of EV specific binding agents or targets 28. The surface chemistry provides a high binding capacity surface, with low levels of non-specific binding. It should be noted that the terms "bind" and "bound" are used to refer to a variety of coupling techniques including adsorption, covalent bonding, non-covalent bonding, chemisorption, and the like.

Any suitable surface chemistry can be used to bind the binding agent 28 to the surface 30 of the optical waveguide biosensor 20. In one implementation, the surface chemistry forms a covalent bond with a primary amine group on the binding agent 28. In another implementation, the surface chemistry binds with biotinylated binding agent 28.

In one implementation, the surface chemistry layer 26 includes poly(ethylene-alt-maleic anhydride) (EMA). EMA uses direct amine coupling to immobilize the binding agent 28 through creation of a covalent bond between an amine group on the binding agent 28 and the surface 30 of the optical waveguide biosensor 20.

In another implementation, the surface chemistry layer 26 includes Streptavidin, which can be used to bind biotinylated molecules to the surface 30 such as, for example, biotinylated versions of the binding agent 28 (the binding agent 28 has biotin attached). Streptavidin has very high affinity binding to biotin that is similar in strength to a covalent bond.

In other implementations, the surface chemistry layer 26 can include any of the surface chemistry described in the patent documents listed at the end of the description.

The optical waveguide biosensor 20 is configured to detect changes in the index of refraction near the top surface 30 of the biosensor 20, which are indicative of a biochemical binding event such as EVs 32 binding to the top surface 30. The optical waveguide biosensor 20 can detect changes in the index of refraction in the area that is about 150-200 nm above the top surface 30. The following is an in-depth description of one implementation where the optical waveguide biosensor 20 is an RWG biosensor.

Figure 4:
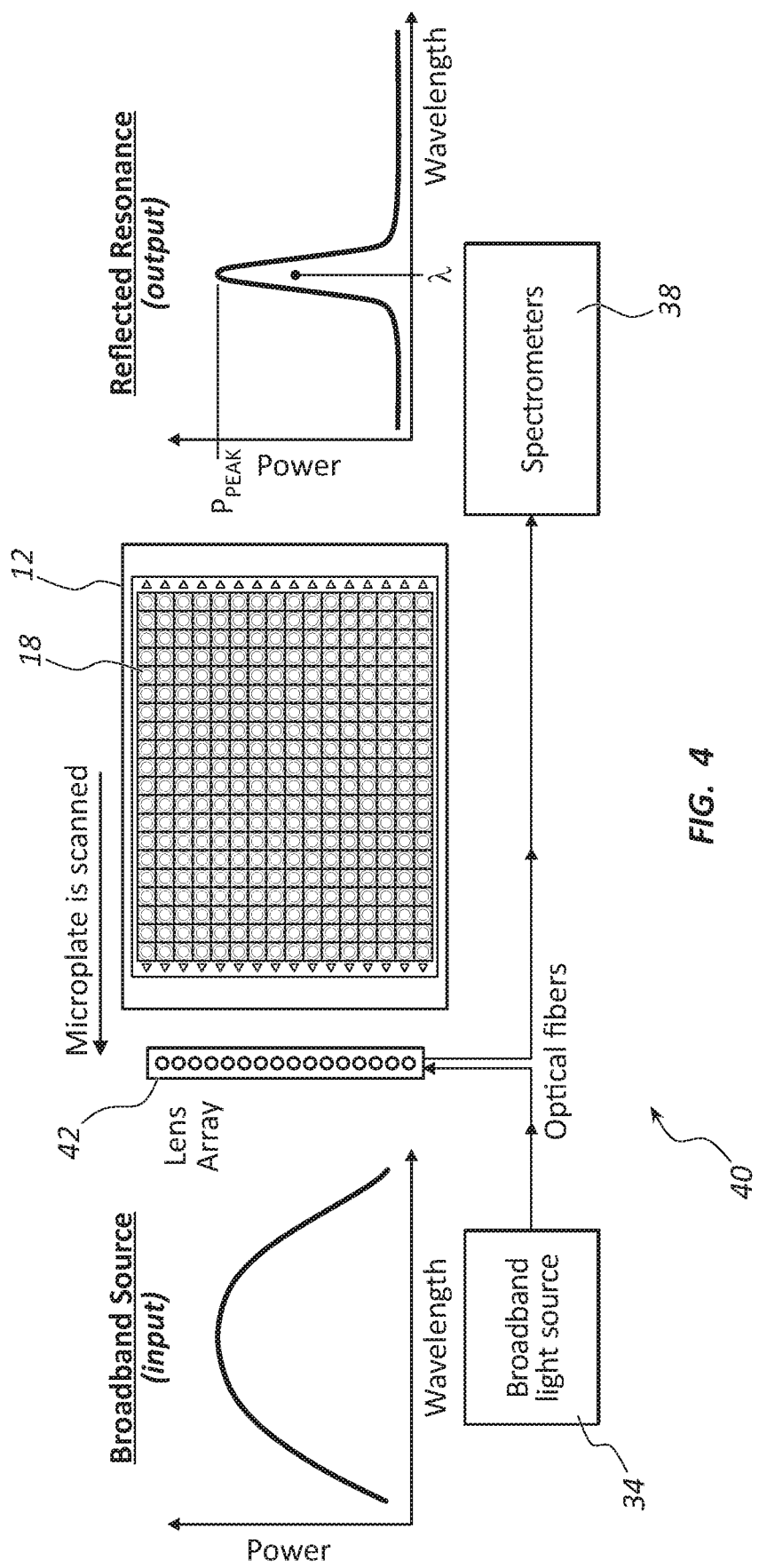
FIG. 4 shows the operation of an optical resonant waveguide grating (RWG) biosensor in accordance with embodiments of the present disclosure.

Referring to FIG. 4, the operation of the optical RWG biosensor 20 is illustrated. A light source 34 illuminates the underside of each RWG biosensor 20 with broadband, polarized light. Light of a specific wavelength (the resonant wavelength) at which a maximal incoupling efficiency is achieved is coupled into and propagates along the waveguide layer 24. This creates an electromagnetic field 36 at the interface of the top surface 30 and the solution that is evanescent in nature, meaning it decays exponentially from the top surface 30. The distance at which it decays to 1/e (e is a numerical constant that is equal to 2.71828) of its initial value is known as the penetration and is a function of the design of the particular RWG biosensor 20, but is typically 150-200 nm.

The resonant light eventually leaks out of the waveguide layer 24 and is reflected back to detectors 38 (alternatively referred to as detection heads or detection units) underneath the RWG biosensor 20. The wavelength of the reflected light is a function of the combined indices of refraction of the materials composing the waveguide and the biomolecules within about 200 nm of the surface 30. When an analyte such as the EVs 32 bind to the surface 30, it changes the local index of refraction, which induces a shift in the wavelength of light that is reflected from the RWG biosensor 20. The wavelength shift is proportional to the amount of the analyte that binds to the surface 30.

The use of the RWG biosensor 20 can provide a number of advantages. One advantage of the RWG biosensor 20 compared to surface plasmon resonance (SPR) biosensors is that light at a nominally normal incident angle can be used to illuminate the RWG biosensor 20. This can be important when sampling large numbers of biosensors simultaneously.

Optical Reader

The optical reader 14 includes a detector system 40 that uses integrated fiber optics to measure shifts in wavelength of the incident light. The detector system 40 includes a series of illumination heads 42 and detection heads 38 arranged in a linear fashion, so that reflection spectra can be collected simultaneously from each well 18 in the microplate 12. The entire microplate 12 can be scanned so that each optical waveguide biosensor 20 is addressed multiple times and each column is addressed in sequence. The wavelengths of the incident light is measured and used to perform the analysis. The optical reader 14 can also include a temperature-controlling unit that serves to reduce or minimize spurious shifts in the incident wavelength due to temperature fluctuations.

The detection heads 38 can include spectrometers configured to measure the wavelength of the reflected light. The spectrometers can also be used to measure the peak power or resonance intensity to determine if the light source 34 is on the optical waveguide sensor 20.

Figure 5:
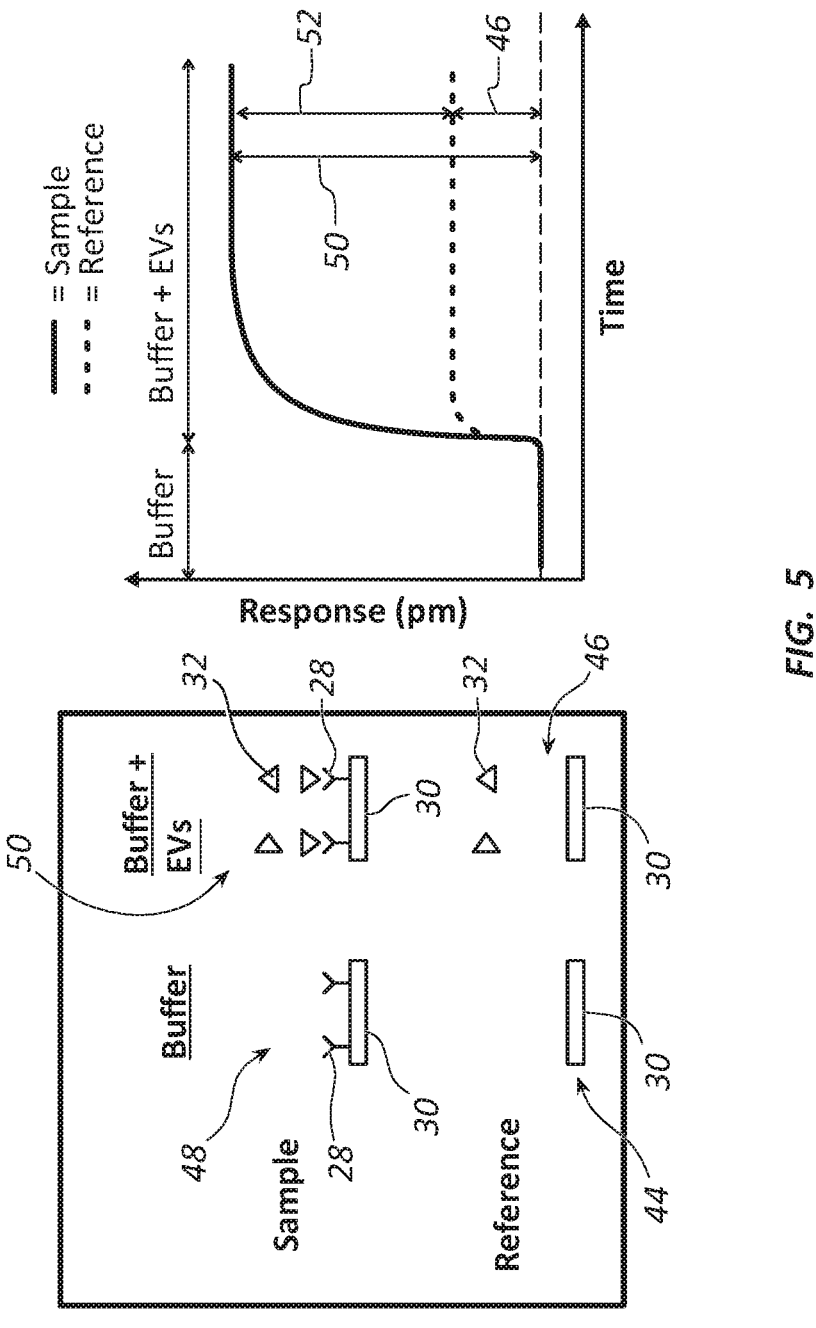
FIG. 5 shows one procedure for analyzing EVs in accordance with embodiments of the present disclosure.

The optical reader 14 can be used to measure the wavelength of reflected light at any of the conditions below (FIG. 5 illustrates the conditions in the left figure). The measurements can be used to create a sample curve and a reference curve, which are also shown in FIG. 5.

Reference wavelength 44—only buffer solution and no immobilized binding agent 28 on the surface 30.

Reference wavelength 46—unbound EVs 32 in buffer solution and no immobilized binding agent 28 on the surface 30.

Sample wavelength 48—only buffer solution and immobilized binding agent 28 on the surface 30.

Sample wavelength 50—bound and unbound EVs 32 in buffer solution and immobilized binding agent 28 on the surface 30.

The wavelength measurements can be used to derive additional information about the EVs 32. For example, an EV binding signal 52 can be determined by subtracting the reference wavelength 46 from the sample wavelength 50. In some implementations, standard wavelengths can be measured and corresponding curves can be created for samples having known quantities of EVs 32. The standard wavelengths can be compared to the sample wavelength 50 to determine the quantity of EVs 32 in a given sample.

EV Analysis Methods

Figure 7:
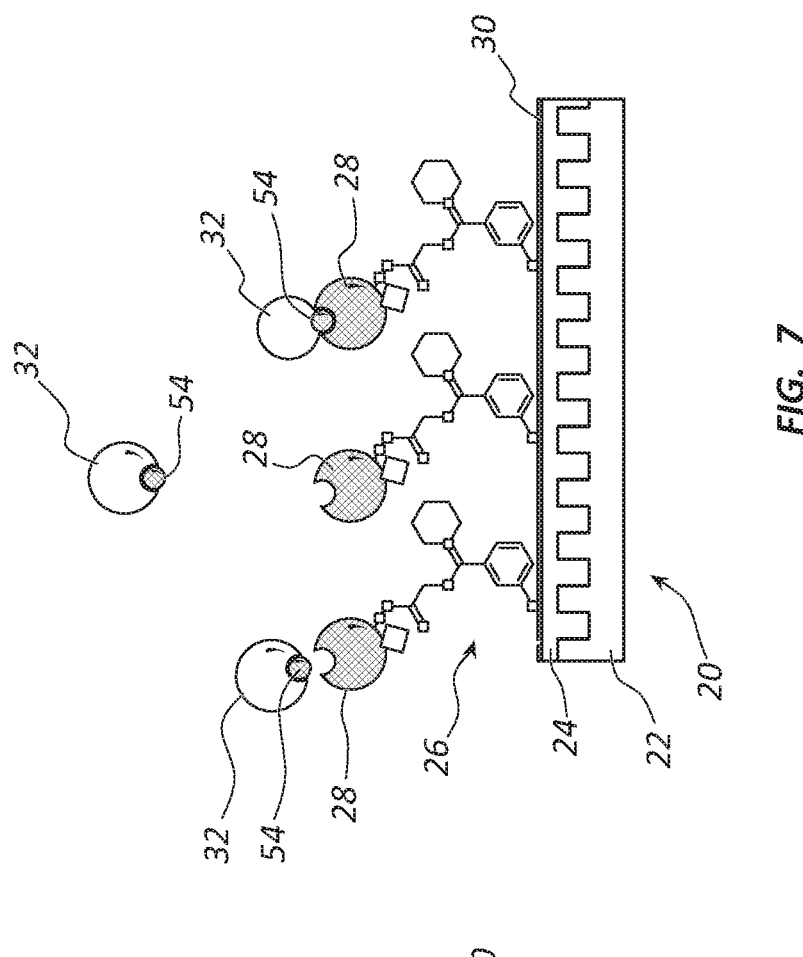
FIG. 7 is a cross-sectional view of an optical waveguide biosensor where a binding agent is bound to an EV and to the surface of the biosensor using a surface chemistry layer including Streptavidin.
Figure 6:
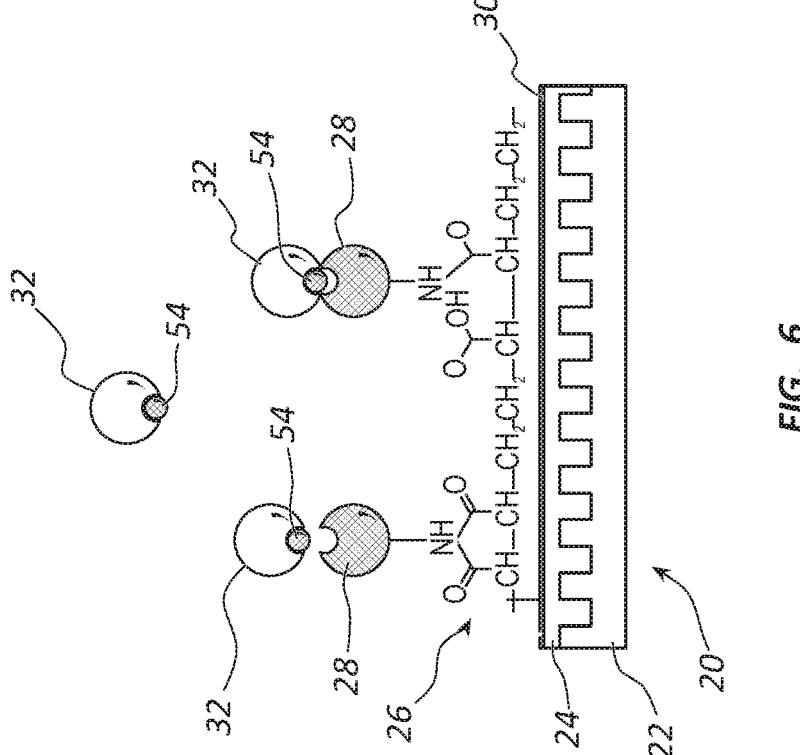
FIG. 6 is a cross-sectional view of an optical waveguide biosensor where a binding agent is bound to an EV and to the surface of the biosensor using a surface chemistry layer including poly(ethylene-alt-maleic anhydride) (EMA).

Referring to FIGS. 6-7, cross-sectional views of the optical waveguide biosensor 20 are shown. The optical waveguide biosensor 20 in FIG. 6 includes poly(ethylene-alt-maleic anhydride) as the surface chemistry layer 26, and the biosensor 20 in FIG. 7 includes Streptavidin as the surface chemistry layer 26.

The surface chemistry layer 26 binds the binding agent 28 to the surface 30 of the optical waveguide biosensor 20. In some implementations, the microplate 12 can be provided with the surface chemistry layer 26 and/or the binding agent 28 already in place. In this situation, the microplate 12 is ready for use immediately upon receipt. In other implementations, the microplate 12 can be provided without the surface chemistry layer 26 and or the binding agent 28 in place. In this situation, the user will need to apply the desired chemistry surface layer 26 and/or the binding agent 28 to the surface 30.

Binding Agent

The binding agent 28 can be any suitable material capable of binding to markers or receptors 54 on the EVs 32. Examples of suitable materials include proteins, antibodies, antibody fragments, and the like. In some implementations, the binding agent 28 can be an antibody or antibody fragment that is specific to a surface marker on the EV 32.

The term "antibody" refers to an immunoglobulin molecule which specifically binds with an antigen. Antibodies can be intact immunoglobulins derived from natural sources or from recombinant sources and can be immunoreactive portions of intact immunoglobulins. Antibodies can be tetramers of immunoglobulin molecules. Tetramers may be naturally occurring or reconstructed from single chain antibodies or antibody fragments.

Antibodies also include dimers that may be naturally occurring or constructed from single chain antibodies or antibody fragments. The antibodies can exist in a variety of forms including, for example, polyclonal antibodies, monoclonal antibodies, Fv, Fab and F(ab')$_2$, as well as single chain antibodies (scFv), humanized antibodies, and human antibodies.

The term "antibody fragment" refers to a portion of an intact antibody and refers to the antigenic determining variable regions of an intact antibody. Examples of antibody fragments include, but are not limited to, Fab, Fab', F(ab')$_2$, Fv fragments, linear antibodies, scFv antibodies, single-domain antibodies, such as camelid antibodies, composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

The term "fragment" refers to a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference.

The binding agent 28 can be selected to bind with specific, membrane-bound receptors 54 on the EVs 32. The EVs 32 can include a variety of different surface molecules that can bind to a variety of EV specific binding agents 28.

Extracellular Vesicles

The term "extracellular vesicle" (EV) refers to small membrane enclosed structures released into the extracellular space by a variety of cell types such as endothelial cells, epithelial cells, platelets, and additionally tumor cells. Typically, at least part of the membrane of the EV 32 is directly obtained from a cell (also known as a donor cell). The EVs 32 can originate from cells by membrane inversion, exocytosis, shedding, blebbing, and/or budding. Depending on the manner of generation (e.g., membrane inversion, exocytosis, shedding, or budding), the EVs 32 may exhibit different surface/lipid characteristics.

The EVs 32 can include heterogeneous compositions of proteins, lipids, nucleic acids, or other biomolecules inside the membranes of EVs 32. The molecular content of the EVs 32 can be representative of its cell of origin including surface and cytoplasmic proteins, messenger RNA, and micro RNAs. The EVs 32 can transport these molecules to a variety of target cells and locations in the body or biological system. The genetic information within the EVs 32 can be transmitted by fusing to the membranes of recipient cells and releasing the genetic information into the inside of the cell.

The EVs 32 can be a variety of sizes. For example, the EVs 32 can have a diameter (or largest dimension where the structure is not spheroid) of 10-5,000 nm, 20-3,000 nm, or 30-2,000 nm. The EVs 32 can also have a diameter (or largest dimension where the structure is not spheroid) of at least 10 nm, at least 20 nm, or at least 30 nm. The EVs 32 can also have a diameter (or largest dimension where the structure is not spheroid) of no more than 5,000 nm, no more than 3,000 nm, or no more than 2,000 nm.

The EVs 32 can be isolated from a variety of biological sources including mammals such as mice, rats, guinea pigs, rabbits, dogs, cats, bovine, horses, goats, sheep, primates, or humans. The EVs 32 can be isolated from biological fluids such as serum, plasma, whole blood, urine, saliva, breast milk, tears, sweat, joint fluid, cerebrospinal fluid, semen, vaginal fluid, ascetic fluid, and amniotic fluid. The EVs 32 can also be isolated from experimental samples such as media taken from cultured cells ("conditioned media", cell media, and cell culture media).

The EVs 32 can also be isolated from tissue samples such as surgical samples, biopsy samples, and cultured cells. When isolating the EVs 32 from tissue sources, it may be beneficial to homogenize the tissue in order to obtain a single cell suspension followed by lysis of the cells to release the EVs 32. When isolating the EVs 32 from tissue samples, homogenization and lysis procedures should be used that do not result in disruption of the EVs 32.

The EVs 32 can be classified into a number of subpopulations based on specific characteristics such as size, biogenesis, cellular origin, protein composition, biological function, and the like. The EVs 32 can be broadly divided into three major subtypes, namely, exosomes, microvesicles (MVs) (also referred to as shedding vesicles), and apoptotic bodies according to their cellular origin as shown in the table below.

TABLE 1

|  | Exosomes | Microvesicles | Apoptotic Bodies |
|---|---|---|---|
| Origin | Endocytic pathway | Plasma membrane | Plasma membrane |
| Size | 30-120 nm | 50-1,000 nm | 500-4,000 nm |
| Function | Intercellular communication | Intercellular communication | Facilitate phagocytosis |
| Markers | Alix, Tsg101, tetraspanins (CD81, CD63, CD9), flotillin | Integrins, selectins, CD40 | Annexin V, phosphatidylserine |

TABLE 1-continued

| | Exosomes | Microvesicles | Apoptotic Bodies |
|---|---|---|---|
| Contents | Proteins and nucleic acids (mRNA, miRNA and other non-coding RNAs) | Proteins and nucleic acids (mRNA, miRNA and other non-coding RNAs) | Nuclear fractions, cell organelles |

Exosomes are typically of endocytic origin and are formed by invagination of the endosomal membrane, which forms vesicles inside the endosomal compartment, generating multivesicular bodies (MVBs). Exosomes are released into the extracellular space when the MVBs fuse with the plasma membrane. Exosomes are typically 30-100 nm in size and have a density of 1.13-1.19 g/ml.

Due to the biogenesis of exosomes, the orientation of the exosomal membrane proteins is similar to that of the plasma membrane. In addition to a similar orientation, the lipid composition of the exosomal membrane is similar to that of the plasma membrane and contains cholesterol, ceramide, and phosphatidylserine (PS) along with several protein markers that can be used to identify exosomes. These include proteins involved in the MVB formation machinery (e.g., Alix and Tsg101), proteins from the membrane and fusion machinery (e.g., GTPases, annexins, and flotillins), and the tetraspanins (CD9, CD63, and CD81). Exosomes can also display saccharide groups on their surface.

The different markers may not be ubiquitously present on all exosomes but are present on a large proportion of exosomes, which is why they are generally accepted as exosomal markers. In addition to the exosomal proteins, exosomes often present a molecular composition that reflects the molecular signature of the parent cells. In some cases, the molecular contents of exosomes may not result from casual sampling of molecules from the parent cell but may arise from an ability to load specific molecules into the exosomes. Exosomes can also contain significant amounts of RNA, including miRNAs, noncoding RNAs, mRNAs, miRNAs, and the like.

Microvesicles are typically formed from outward budding of the plasma membrane, releasing the MVs directly into the extracellular space. Some MVs present PS in the outer leaflet of the membrane and this feature can be used to isolate and identify MVs in biological samples. MVs can include markers such as the CD40 ligand, adenosine diphosphate ribosylation factor 6, and certain integrins and selectins. The intravesicular content of MVs can include membrane and cytosolic proteins, mRNAs, miRNAs, and the like. MVs can be 50-1,000 nm in size.

Apoptotic bodies are typically released when cells become apoptotic and they are formed by blebbing of the plasma membrane, which releases the apoptotic bodies directly into the extracellular space. Similar to the other subtypes of the EVs 32, apoptotic bodies present PS in the outer leaflet of the lipid bilayer. In addition, they present thrombospondin and complement component C3b, which can be used to identify apoptotic bodies. Furthermore, apoptotic bodies can be distinguished from the other EV subtypes by containing organelles, DNA fragments, and histones as part of the intravesicular cargo in addition to proteins and other molecules from the cytosol of the parent cell. Apoptotic bodies can be 500-4,000 nm in size and have a density of 1.16-1.28 g/ml.

The terms "microRNA," "miRNA," or "miR" refer to RNAs that function post-transcriptionally to regulate expression of genes, typically by binding to complementary sequences in the three prime (3') untranslated regions (3' UTRs) of target messenger RNA (mRNA) transcripts, usually resulting in gene silencing. miRNAs are typically small regulatory RNA molecules, for example, 21 or 22 nucleotides long (no more than 100 nucleotides long, or no more than 50 nucleotides long). The terms "microRNA," "miRNA," and "miR" are used interchangeably.

EV Isolation

The EVs 32 can be isolated from a sample using the following procedure. If the binding agent 28 is not already attached to the microplate 12, then the first step is to attach the binding agent 28. This can be done by adding an immobilization buffer solution containing the binding agent 28 to each of the wells 18 and incubating the microplate 12 until the binding agent 28 is immobilized on the surface chemistry layer 26.

The immobilization buffer solution is removed and replaced with a blocking buffer solution that deactivates any remaining immobilization sites on the surface chemistry layer 26. The blocking buffer solution is removed and the wells 18 are rinsed. The microplate 12 is now ready to receive and analyze samples containing the EVs 32.

The samples containing the EVs 32 are positioned in the wells 18. The EVs 32 bind to the binding agent 28, which is bound to the surface 30 of the biosensor 20 in the manner shown in FIGS. 6-7. The remaining content of the samples is flushed from the wells 18 leaving only the bound EVs 32 on the microplate 12. In this manner, the bound EVs 32 can be isolated and phenotyped based on the presence of a marker capable of binding to the binding agent 28. And, all of this can be done in a single step.

EV Quantification

The quantity of the EVs 32 in a given sample can be determined by measuring the wavelength of the sample and comparing it to one or more standard wavelengths obtained from samples having a known concentration of the same EVs 32. Procedures for measuring the standard wavelengths of samples having a known concentration of the EVs 32 and comparing them to the wavelength measured for samples having an unknown concentration of the EVs 32 are described above.

EV Second Level Phenotyping

Figure 8:
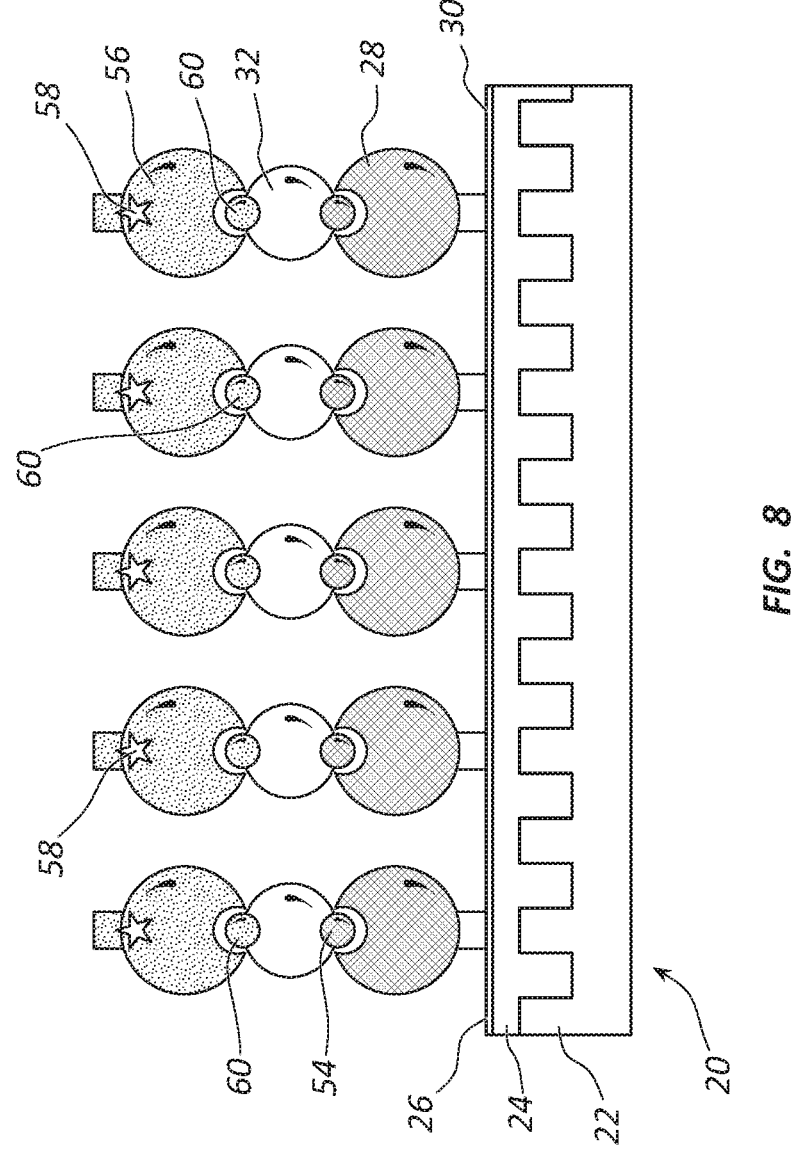
FIG. 8 is a cross-sectional view of an optical waveguide biosensor where bound EVs have been further characterized by being bound to a labeled ligand.

Referring to FIG. 8, the bound EVs 32 can be further separated and classified using one or more labeled or tagged ligands 56 configured to bind to another marker or receptor 60 on the EVs 32. The ligands 56 can include any suitable type of label or tag 58. For example, the ligands 56 can include a fluorescent label, a colorimetric label, or a luminescent label.

The ligands 56 can be any suitable protein, compound, molecule, or the like that is capable of binding to a specific marker on the EVs 32. In some implementations, the ligands 56 can be any of the antibodies described above in connection with the binding agent 28 or the EVs 32. In some implementations, two, three, four, or more different ligands 56 each having a different label 58 can be used to further separate and classify the EVs 32.

The number of the EVs 32 bound to a given ligand 56 can be quantified using the same techniques described above in connection with the bound EVs 32. Namely, standard wavelength measurements can be obtained using samples having known quantities of the relevant EVs 32 and compared to the wavelength measurements of the labeled EVs 32.

EV Intravesicular Content

Figure 9:
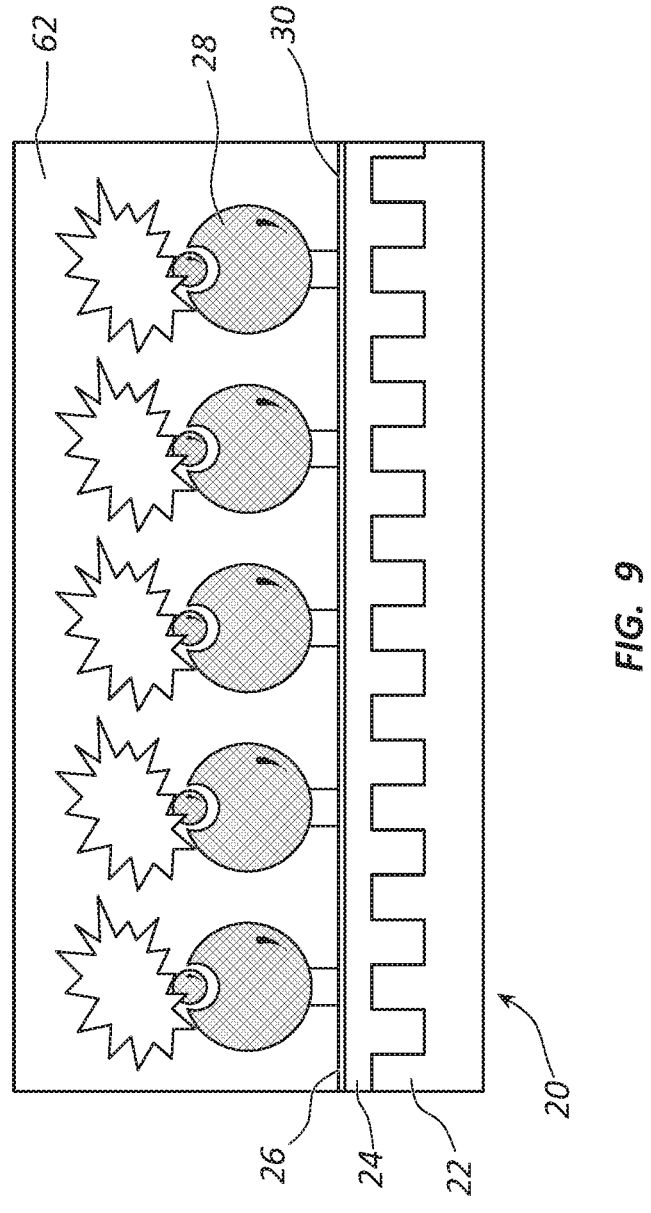
FIG. 9 is a cross-sectional view of an optical waveguide biosensor where the bound EVs have been ruptured so that the intravesicular contents can be analyzed.

Referring to FIG. 9, the intravesicular content of the bound EVs 32 can be analyzed using the following procedure. A reagent 62 can be added to the wells 18 to rupture or lyse the EVs 32 and expose their contents for further analysis. Any suitable reagent 62 can be used to rupture the EVs 32. In some implementations, the reagent 62 is a lysing reagent such as TRIzol lysing reagent.

The intravesicular content of the EVs 32 can include proteins, DNA, RNA (micro RNA), and the like. These molecules can be removed to another vessel and extracted by completing the standard phase extraction protocol. These molecules can be analyzed to diagnose a disease, determine the prognosis of a disease, and the like.

The methods for analyzing the EVs 32 can provide a number of advantages. One advantage is that the technology can be used to isolate, quantify, and phenotype the EVs 32 directly from complex biological samples such as bodily fluids—e.g., blood serum, cell culture medium, urine, and the like—without any intermediate purification steps.

EV Analysis Kit

A kit for analyzing the EVs 32 can include any of the materials and components described above. In one implementation, the kit can include the microplate 12 and at least one of the labeled ligand 56 or the reagent 62. In other implementations, the kit can include packaging that is configured to hold the components of the kit together or indicate that the components are part of the kit.

EXAMPLES

The following examples are provided to further illustrate the disclosed subject matter. They should not be used to constrict or limit the scope of the claims in any way.

Example 1

In this Example, the quantity of extracellular vesicles (EVs) having a specific biomarker in a sample is analyzed using the Corning Epic system, which is a label-free, high throughput screening system. The system includes a biosensor microplate having 384 sample wells. Each sample well has an optical resonant waveguide grating biosensor (RWG biosensor) positioned in the bottom. The RWG biosensor includes a nanometer scale optical grating embedded in a substrate and a high-refractive index waveguide layer or coating applied to the substrate. The system also includes an optical reader that illuminates the RWG biosensors with a broadband light source.

Light at the resonant wavelength is coupled into and propagates along the waveguide layer. The evanescent field created by the resonant coupling of the light penetrates approximately 150 nm into the layer above the RWG biosensors probing the local refractive index. The resonant wavelength is detected with a CMOS camera after it is outcoupled from the RWG biosensors. The resonant wavelength of the light shifts due to changes in the refractive index in the sensing zone caused by EVs binding to the RWG biosensors.

The RWG biosensors include a surface chemistry layer on the top surface. The surface chemistry layer includes polyethylene-maleic anhydride (EMA), which immobilizes an antibody on the RWG biosensors by creating a covalent bond between an amine group on the antibody and the top surface.

An array of EV specific antibodies is created in the wells of the microplate as follows. The antibodies are diluted in a buffer solution and added to most of the wells in the microplate. A control buffer solution is added to the remaining wells to form buffer only control wells that are used to quantify the antibody immobilization level. The microplate is incubated to facilitate immobilization of the antibodies on the top surface of the RWG biosensors. The buffer solution is removed and replaced with a blocking buffer solution that deactivates any remaining immobilization sites. The blocking buffer is removed and the wells are rinsed.

EVs having are bound to the RWG biosensors as follows. A fresh cell culture medium without serum is added to the wells. The microplate is loaded into the optical reader and allowed to equilibrate for approximately 2 hours to stabilize the sensors. The resonant wavelengths of the wells are measured to create a baseline. Cell culture mediums containing a known quantity of EVs having a specific marker and cell culture mediums containing an unknown quantity of the same EVs are added to the antibody immobilized wells with some of the wells being left without any EVs to serve as controls. The microplate is incubated for approximately 1 hour to allow binding of the EVs to the antibodies. The resonant wavelengths of the wells are measured.

A standard curve is created using the measurements of the cell culture medium with a known quantity of EVs and the controls. The quantity of EVs having the marker in the unknown cell culture medium is determined by comparing the standard curve to the curve created using the cell culture medium having an unknown quantity of the EVs.

Example 2

In this Example, additional phenotype information for the EVs is obtained using the Corning Epic system and labeled antibodies. The EVs are bound to the RWG biosensors and analyzed in the manner described an Example 1. After measuring the resonant wavelength of the wells containing bound EVs, the medium is removed from the wells and a buffer solution containing fluorescent labeled antibodies is added (this example could be repeated using colorimetric or luminescent labels). The labeled antibodies bind to a second marker or epitope of certain EVs. The labeled antibodies provide additional phenotype information about the EVs through the identification of other surface markers including those that could potentially be markers to specific diseases. The quantity of bound EVs having the second marker is determined by creating a standard curve in the manner described in Example 1 and comparing it to the curve created using the cell culture medium having an unknown quantity of EVs having the same marker.

Example 3

In this Example, additional phenotype information is obtained by examining the intravesicular content of the EVs. The EVs are bound to the RWG biosensors and analyzed in the manner described an Example 1 or Example 2. The EVs are lysed by adding TRIzol reagent (monophasic solution of phenol and guanidine isothiocyanate) to the bound EVs in the wells. This release the intravesicular content of the EVs, which includes proteins, DNA, RNA (e.g., miRNA), and the like. The contents of the wells are removed to another vessel and separated by following standard phase extraction protocol. The miRNA is analyzed to diagnose a disease and/or determine the prognosis of a disease.

Illustrative Implementations

The following is a description of various implementations of the disclosed subject matter. Each implementation may include one or more of the various features, characteristics, or advantages of the disclosed subject matter. The implementations are intended to illustrate a few aspects of the disclosed subject matter and should not be considered a comprehensive or exhaustive description of all possible implementations.

P1. A method comprising: positioning a sample on an optical waveguide biosensor, the sample including extracellular vesicles; binding the extracellular vesicles to the optical waveguide biosensor; detecting the extracellular vesicles bound to the optical waveguide biosensor; and analyzing a characteristic of the extracellular vesicles bound to the optical waveguide biosensor.

P2. The method of paragraph P1 wherein the characteristic of the extracellular vesicles includes the number of extracellular vesicles in the sample.

P3. The method of any one of paragraphs P1-P2 wherein the characteristic of the extracellular vesicles includes the size of the extracellular vesicles in the sample.

P4. The method of any one of paragraphs P1-P3 wherein the characteristic of the extracellular vesicles includes the type of extracellular vesicles in the sample.

P5. The method of any one of paragraphs P1-P4 wherein analyzing the characteristic of the extracellular vesicles comprises binding ligand(s) to the extracellular vesicles.

P6. The method of paragraph P5 wherein the ligands include a first ligand that binds to a first marker on the extracellular vesicles and a second ligand that binds to a second marker on the extracellular vesicles.

P7. The method of any one of paragraphs P5-P6 comprising binding the ligands to the extracellular vesicles while the extracellular vesicles are bound to the optical waveguide biosensor.

P8. The method of any one of paragraphs P5-P7 wherein the ligands include a label.

P9. The method of paragraph P8 wherein the label is a fluorescent label.

P10. The method of any one of paragraphs P8-P9 wherein the label is a colorimetric label.

P11. The method of any one of paragraphs P8-P10 wherein the label is a luminescent label.

P12. The method of any one of paragraphs P1-P11 wherein analyzing the characteristic of the extracellular vesicles comprises analyzing the intravesicular content of the extracellular vesicles.

P13. The method of paragraph P12 wherein analyzing the intravesicular content of the extracellular vesicles comprises analyzing protein, RNA, and/or DNA in the intravesicular content.

P14. The method of any one of paragraphs P12-P13 wherein analyzing the intravesicular content of the extracellular vesicles comprises analyzing the composition of the intravesicular content.

P15. The method of any one of paragraphs P12-P14 wherein analyzing the intravesicular content of the extracellular vesicles comprises rupturing the extracellular vesicles.

P16. The method of paragraph P15 comprising rupturing the extracellular vesicles while the extracellular vesicles are bound to the optical waveguide biosensor.

P17. The method of any one of paragraphs P12-P16 wherein analyzing the intravesicular content of the extracellular vesicles comprises lysing the extracellular vesicles.

P18. The method of paragraph P17 comprising lysing the extracellular vesicles while the extracellular vesicles are bound to the optical waveguide biosensor.

P19. The method of any one of paragraphs P1-P18 wherein the sample is an unpurified biological sample.

P20. The method of any one of paragraphs P1-P19 wherein the sample is an unpurified bodily fluid.

P21. The method of any one of paragraphs P1-P20 wherein detecting the extracellular vesicles comprises illuminating the optical waveguide biosensor and detecting a change in a resonant wavelength of light reflected from the optical waveguide biosensor.

P22. The method of any one of paragraphs P1-P21 comprising binding a binding agent to the optical waveguide biosensor and binding the extracellular vesicles to the binding agent.

P23. The method of paragraph P22 wherein the binding agent includes an antibody.

P24. The method of any one of paragraphs P1-P23 wherein the optical waveguide biosensor is an optical resonant waveguide grating biosensor.

P25. A system for analyzing extracellular vesicles comprising: an optical waveguide biosensor; extracellular vesicles bound to the optical waveguide biosensor; and a ligand bound to the extracellular vesicles, the ligand including a label.

P26. The system of paragraph P25 wherein the ligand includes an antibody configured to bind to a marker on the extracellular vesicles.

P27. The system of any one of paragraphs P25-P26 wherein the ligand is a first ligand and the label is a first label, the system comprising a second ligand bound to the extracellular vesicles, the second ligand including a second label.

P28. The system of paragraph P27 wherein the first ligand is configured to bind to one marker on the extracellular vesicles and the second ligand is configured to bind to another marker on the extracellular vesicles.

P29. The system of any one of paragraphs P25-P28 wherein the label is a fluorescent label.

P30. The system of any one of paragraphs P25-P29 wherein the label is a colorimetric label.

P31. The system of any one of paragraphs P25-P30 wherein the label is a luminescent label.

P32. The system of any one of paragraphs P25-P31 comprising an optical reader configured to detect the extracellular vesicles bound to the optical waveguide biosensor.

P33. The system of paragraph P32 wherein the optical reader includes a light source configured to illuminate the optical waveguide biosensor.

P34. The system of paragraph P33 wherein the light source is broadband light source.

P35. The system of any one of paragraphs P25-P34 comprising an optical reader configured to illuminate the optical waveguide biosensor and detect a change in a resonant wavelength of light reflected from the optical waveguide biosensor.

P36. The system of any one of paragraphs P25-P35 wherein the optical waveguide biosensor is an optical resonant waveguide grating biosensor.

P37. The system of any one of paragraphs P25-P36 wherein the extracellular vesicles are exosomes.

P38. The system of any one of paragraphs P25-P37 wherein the extracellular vesicles are microvesicles.

P39. The system of any one of paragraphs P25-P38 wherein the extracellular vesicles are apoptotic bodies.

P40. The system of any one of paragraphs P25-P39 comprising: a plurality of the optical waveguide biosensors; and a microplate including a plurality of wells, each of the plurality of wells including at least one of the plurality of optical waveguide biosensors.

P41. The system of paragraph P40 wherein the microplate includes at least 24 of the wells.

P42. The system of paragraph P40 wherein the microplate includes at least 96 of the wells.

P43. The system of paragraph P40 wherein the microplate includes at least 384 of the wells.

P44. A system for analyzing extracellular vesicles comprising: a microplate including a plurality of wells; an optical waveguide biosensor positioned in each of the plurality of wells; and a sample positioned in each of the plurality of wells; wherein the samples each include the intravesicular content of ruptured extracellular vesicles that were bound to the optical waveguide biosensors.

P45. The system of paragraph P44 wherein the samples each include the intravesicular content of lysed extracellular vesicles that were bound to the optical waveguide biosensors.

P46. The system of any one of paragraphs P44-P45 wherein the samples include a lysing reagent.

P47. The system of any one of paragraphs P44-P46 wherein the intravesicular content of the ruptured extracellular vesicles comprises proteins, RNA, and/or DNA.

P48. The system of any one of paragraphs P44-P47 comprising an optical reader configured to detect the extracellular vesicles that were bound to the optical waveguide biosensor.

P49. The system of paragraph P48 wherein the optical reader includes a light source configured to illuminate the optical waveguide biosensor.

P50. The system of paragraph P49 wherein the light source is a broadband light source.

P51. The system of any one of paragraphs P44-P50 comprising an optical reader configured to illuminate the optical waveguide biosensor and detect a change in a resonant wavelength of light reflected from the optical waveguide biosensor.

P52. The system of any one of paragraphs P44-P51 wherein the optical waveguide biosensor is an optical resonant waveguide grating biosensor.

P53. The system of any one of paragraphs P44-P52 wherein the ruptured extracellular vesicles are exosomes.

P54. The system of any one of paragraphs P44-P53 wherein the ruptured extracellular vesicles are microvesicles.

P55. The system of any one of paragraphs P44-P54 wherein the ruptured extracellular vesicles are apoptotic bodies.

P56. The system of any one of paragraphs P44-P55 wherein the microplate includes at least 24 of the wells.

P57. The system of any one of paragraphs P44-P56 wherein the microplate includes at least 96 of the wells.

P58. The system of any one of paragraphs P44-P57 wherein the microplate includes at least 384 of the wells.

P59. A kit for analyzing extracellular vesicles comprising: a microplate including a plurality of wells; an optical waveguide biosensor positioned in each of the plurality of wells; binding agents bound to each of the optical waveguide biosensors, the binding agents being configured to bind to extracellular vesicles; and at least one of: (a) ligands configured to bind to the extracellular vesicles, the ligands including a label; or (b) a reagent configured to rupture the extracellular vesicles.

P60. The kit of paragraph P59 wherein the binding agents bound to each of the optical waveguide biosensors include antibodies configured to bind to a marker on the extracellular vesicles.

P61. The kit of any one of paragraphs P59-P60 wherein the ligands include a first ligand configured to bind to a first marker on the extracellular vesicles and a second ligand configured to bind to a second marker on the extracellular vesicles.

P62. The kit of any one of paragraphs P59-P61 wherein the reagent includes a lysing reagent configured to lyse the extracellular vesicles.

P63. The kit of any one of paragraphs P59-P62 comprising both (a) and (b).

P64. The kit of any one of paragraphs P59-P63 comprising an optical reader configured to detect the extracellular vesicles bound to the optical waveguide biosensors.

P65. The kit of any one of paragraphs P59-P64 comprising packaging designating the microplate and at least one of (a) or (b) as being a unit.

P66. The kit of any one of paragraphs P59-P65 comprising packaging holding the microplate and at least one of (a) or (b) together as a unit.

P67. The kit of any one of paragraphs P59-P66 wherein the optical waveguide biosensor is an optical resonant waveguide grating biosensor.

P68. The kit of any one of paragraphs P59-P67 wherein the extracellular vesicles are exosomes.

P69. The kit of any one of paragraphs P59-P68 wherein the extracellular vesicles are microvesicles.

P70. The kit of any one of paragraphs P59-P69 wherein the extracellular vesicles are apoptotic bodies.

P71. The kit of any one of paragraphs P59-P70 wherein the microplate includes at least 24 of the wells.

P72. The kit of any one of paragraphs P59-P71 wherein the microplate includes at least 96 of the wells.

P73. The kit of any one of paragraphs P59-P72 wherein the microplate includes at least 384 of the wells.

General Terminology and Interpretative Conventions

Any methods described in the claims or specification should not be interpreted to require the steps to be performed in a specific order unless expressly stated otherwise. Also, the methods should be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items.

The terms have, having, include, and including should be interpreted to be synonymous with the terms comprise and comprising. The use of these terms should also be understood as disclosing and providing support for narrower alternative implementations where these terms are replaced by "consisting" or "consisting essentially of."

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should be construed in light of the number of recited significant digits and by applying ordinary rounding techniques.

All disclosed ranges are to be understood to encompass and provide support for claims that recite any subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth), which values can be expressed alone or as a minimum value (e.g., at least 5.8) or a maximum value (e.g., no more than 9.9994).

All disclosed numerical values are to be understood as being variable from 0-100% in either direction and thus provide support for claims that recite such values (either alone or as a minimum or a maximum—e.g., at least <value> or no more than <value>) or any ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range expressed individually (e.g., 15.2), as a minimum value (e.g., at least 4.3), or as a maximum value (e.g., no more than 12.4).

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean,"

etc.). References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

INCORPORATION BY REFERENCE

The entire contents of each of the documents listed below are incorporated by reference into this document. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Pat. No. 4,815,843 (application Ser. No. 07/019,557), titled "Optical Sensor for Selective Detection of Substances and/or for the Detection of Refractive Index Changes in Gaseous, Liquid, Solid and Porous Samples," filed on 29 May 1986, issued on 28 Mar. 1989.

U.S. Pat. No. 5,738,825 (application Ser. No. 08/854,586), titled "Optical Biosensor Matrix," filed on 18 Jul. 1994, issued on 14 Apr. 1998.

U.S. Pat. No. 7,057,720 (application Ser. No. 10/602,304), titled "Optical Interrogation System and Method for Using Same," filed on 24 Jun. 2003, issued on 6 Jun. 2006.

U.S. Pat. No. 7,136,550 (application Ser. No. 10/977,520), titled "Single-Fiber Launch/Receive System for Biosensing Applications," filed on 28 Oct. 2004, issued on 14 Nov. 2006.

U.S. Pat. No. 7,203,386 (application Ser. No. 10/947,021), titled "Self-Referencing Waveguide Grating Sensors," filed on 21 Sep. 2004, issued on 10 Apr. 2007.

U.S. Pat. No. 7,239,395 (application Ser. No. 10/856,572), titled "Optical Interrogation Systems with Reduced Parasitic Reflections and a Method for Filtering Parasitic Reflections," filed on 27 May 2004, issued on 3 Jul. 2007.

U.S. Pat. No. 7,286,221 (application Ser. No. 11/019,439), titled "Arrayed Sensor Measurement System and Method," filed on 21 Dec. 2004, issued on 23 Oct. 2007.

U.S. Pat. No. 7,292,333 (application Ser. No. 11/100,199), titled "Optical Interrogation System and Method for 2-D Sensor Arrays," filed on 5 Apr. 2005, issued on 6 Nov. 2007.

U.S. Pat. No. 7,346,233 (application Ser. No. 11/058,155), titled "Single Mode (SM) Fiber Optical Reader System and Method for Interrogating Resonant Waveguide-Grating Sensor(s)," filed on 14 Feb. 2005, issued on 18 Mar. 2008.

U.S. Pat. No. 7,604,984 (application Ser. No. 11/027, 547), titled "Spatially Scanned Optical Reader System and Method for Using Same," filed on 29 Dec. 2004, issued on 20 Oct. 2009.

U.S. Pat. No. 8,114,348 (application Ser. No. 12/480, 886), titled "Label-Free High Throughput Biomolecular Screening System and Method," filed on 9 Jun. 2009, issued on 14 Feb. 2012.

U.S. Pat. Pub. No. 2006/0110594 (application Ser. No. 10/996,952), titled "Polymer-Coated Substrates for Binding Biomolecules and Methods of Making and Using Thereof," filed on 24 Nov. 2004, published on 25 May 2006.

U.S. Pat. Pub. No. 2006/0141527 (application Ser. No. 11/027,509), titled "Method for Creating a Reference Region and a Sample Region on a Biosensor and the Resulting Biosensor," filed on 29 Dec. 2004, published on 29 Jun. 2006.

The invention claimed is:

1. A method comprising:

positioning a sample on an optical waveguide biosensor, the sample including extracellular vesicles;

binding the extracellular vesicles to the optical waveguide biosensor;

detecting the extracellular vesicles bound to the optical waveguide biosensor; and analyzing a characteristic of the extracellular vesicles bound to the optical waveguide biosensor;

wherein binding the extracellular vesicles to the optical waveguide biosensor comprises using a binding agent specific to a marker on the extracellular vesicles to bind the extracellular vesicles to a surface of the optical waveguide biosensor.

2. The method of claim 1, wherein the characteristic of the extracellular vesicles includes the number of extracellular vesicles in the sample, the size of extracellular vesicles in the sample, and/or the type of extracellular vesicles in the sample.

3. The method of claim 1, wherein analyzing the characteristic of the extracellular vesicles comprises binding ligands to the extracellular vesicles.

4. The method of claim 3, wherein the ligands include a first ligand that binds to a first marker on the extracellular vesicles and a second ligand that binds to a second marker on the extracellular vesicles.

5. The method of claim 1, wherein analyzing the characteristic of the extracellular vesicles comprises analyzing the intravesicular content of the extracellular vesicles.

6. The method of claim 5, wherein analyzing the intravesicular content of the extracellular vesicles comprises analyzing protein, RNA, and/or DNA in the intravesicular content.

7. The method of claim 5, wherein analyzing the intravesicular content of the extracellular vesicles comprises lysing the extracellular vesicles.

8. The method of claim 1, wherein the sample is an unpurified biological sample.

9. The method of claim 1, wherein detecting the extracellular vesicles comprises illuminating the optical waveguide biosensor and detecting a change in a resonant wavelength of light reflected from the optical waveguide biosensor.

10. The method of claim 1, wherein the optical waveguide biosensor is an optical resonant waveguide grating biosensor.

11. A system for analyzing extracellular vesicles comprising:

an optical waveguide biosensor;

extracellular vesicles bound to the optical waveguide biosensor; and a ligand bound to the extracellular vesicles, the ligand including a label;

wherein the extracellular vesicles are bound to the optical waveguide biosensor with a binding agent specific to a marker on the extracellular vesicles, and wherein the binding agent binds to a surface chemistry layer on the optical waveguide biosensor for attachment and immobilization of the binding agent; and wherein the marker and the label are different from each other.

12. The system of claim 11, wherein the ligand is a first ligand and the label is a first label, the system comprising a second ligand bound to the extracellular vesicles, the second ligand including a second label.

13. The system of claim 12, wherein the first ligand is configured to bind to one marker on the extracellular vesicles and the second ligand is configured to bind to another marker on the extracellular vesicles.

14. The system of claim 11, comprising an optical reader configured to detect the extracellular vesicles bound to the optical waveguide biosensor.

15. The system of claim 11, comprising:

a plurality of the optical waveguide biosensors; and a microplate including a plurality of wells, each of the plurality of wells including at least one of the plurality of optical waveguide biosensors.

16. The system of claim 11, further comprising a lysing reagent.

17. The system of claim 11, wherein the extracellular vesicles comprise proteins, RNA, and/or DNA inside the extracellular vesicles.

18. A kit for analyzing extracellular vesicles comprising:

a microplate including a plurality of wells;

an optical waveguide biosensor positioned in each of the plurality of wells;

binding agents specific to a marker on the extracellular vesicles and bound to surface chemistry layer of each of the optical waveguide biosensors, the binding agents being configured to bind the marker on the extracellular vesicles; and at least one of:

(a) ligands configured to bind to the extracellular vesicles, the ligands including a label, and wherein the marker and the label are different from each other; or (b) a reagent configured to rupture the extracellular vesicles.

19. The kit of claim 18, wherein the ligands comprise a first ligand including a first label and a second ligand including a second label, wherein the first ligand is configured to bind to a first marker on the extracellular vesicles and the second ligand is configured to bind to a second marker on the extracellular vesicles.

* * * * *